United States Patent
Kis et al.

(10) Patent No.: US 6,776,982 B2
(45) Date of Patent: *Aug. 17, 2004

(54) AUTOCLAVABLE PHARMACEUTICAL COMPOSITIONS CONTAINING A CHELATING AGENT

(75) Inventors: Gyorgy Lajos Kis, Triboltingen (CH); Marcia Johanna Adam, Gisikon (CH); Andrea Fetz, Wetzikon (CH)

(73) Assignee: Novartis AG, Basel (CH)

(*) Notice: Subject to any disclaimer, the term of this patent is extended or adjusted under 35 U.S.C. 154(b) by 0 days.

This patent is subject to a terminal disclaimer.

(21) Appl. No.: 10/016,361

(22) Filed: Dec. 10, 2001

(65) Prior Publication Data

US 2002/0165254 A1 Nov. 7, 2002

Related U.S. Application Data

(62) Division of application No. 09/616,151, filed on Jul. 14, 2000, now Pat. No. 6,468,548, which is a continuation of application No. PCT/EP99/00160, filed on Jan. 13, 1999.

(30) Foreign Application Priority Data

Jan. 15, 1998 (EP) .......................................... 98810016

(51) Int. Cl.⁷ ............................................. A61K 31/74
(52) U.S. Cl. .................................................. 424/78.04
(58) Field of Search .............................. 424/400, 78.04

(56) References Cited

U.S. PATENT DOCUMENTS

| | | | |
|---|---|---|---|
| 5,165,918 A | | 11/1992 | Heyl et al. |
| 5,576,311 A | | 11/1996 | Guy |
| 5,624,893 A | * | 4/1997 | Yanni ........................... 514/12 |
| 5,679,665 A | | 10/1997 | Bergamini et al. |
| 6,395,756 B2 | * | 5/2002 | Trimming et al. .......... 514/324 |
| 6,455,547 B1 | * | 9/2002 | Kis ............................. 514/324 |

FOREIGN PATENT DOCUMENTS

| | | | |
|---|---|---|---|
| EP | 0 258 865 | | 9/1987 |
| EP | 0 719 545 | | 7/1991 |
| GB | 1 399 834 | | 7/1975 |
| GB | 2 001 529 | | 2/1979 |
| JP | 62 277323 | | 12/1987 |
| JP | 62277323 A | * | 12/1987 ......... A61K/31/445 |
| JP | 73 324034 | | 12/1995 |
| JP | 62277323 | | 12/1998 |
| WO | WO 97/00669 | | 1/1997 |

OTHER PUBLICATIONS

International Search Report PCT/EP 99/00160, filed Jan. 13, 1999.
Search Report EP 01124282.
Abstract, JP 7324034, Published Dec. 12, 1995.
European Search Report.
Fujita et al., Rinsho Iyaku [Journal of Clinical Therapeutic and Medicines], vol. 5(4), "Clinical Efficacy and Optimal Concentration of Ketotifen Ophthalmic on allergic Conjunctivitus and Vernal Conjunctivitus", pp. 709–721, (1989) [English translation].
Kawasaki et al., Iyakuhin Kenkyu, vol. 19(5), "Eye Irritation Study on Ketotifen Fumarate–Containing Eye Drops in Rabbits (I) Eye Irritability on Single or Frequent Topical Instillation", pp. 821–826, (1988) [English Translation].
Kawasaki et al., Iyakuhin Kenkyu, vol. 19(5), "Eye Irritation study on Ketotifen Fumarate–Containing Eye Drops in Rabbits (II) Eye Irritability on Successive Four–Week or Thirteen Week Instillations", pp. 827–838, (1988) [English translation].
Mikuni et al., Ringan [Japanese Journal of Clinical Ophthalmology], vol. 36(6), "Quantitative Therapeutic Efficacy of Ketotifen Eye Drops for Allergic Conjunctivitis", pp. 573–576, (1982) [English translation].
Mikuni et al., Rinsho Iyaku [Journal of Clinical Therapeutic and Medicines], vol. 4(12), "Evaluation of Ketotifen Ophthalmic Solution on Efficacy and Safety on Allergic Conjunctivitis and Vernal Conjunctivitis—Result on Multiclinic Open Trial—", pp. 2371–2383, (1988) [English translation].
Mikuni et al., Tokai J Exp Clin Med., vol. 9, No. 1, "A Quantitative Tear Fluids Determination of Therapeutic Efficacy for Allergic Conjunctivitis", pp. 35–41, (1984).
Nakayasu et al., Rinsho Iyaku Journal of Clinical Therapeutic and Medicines, vol. 4(12), "Safety of Ketotifen Ophthalmic Solution on Ocular External and Front Region", pp. 2357–2369, (1988) [English translation].

* cited by examiner

Primary Examiner—Thurman K. Page
Assistant Examiner—Robert M. Joynes
(74) Attorney, Agent, or Firm—Susan Hess

(57) ABSTRACT

Disclosed are ophthalmic compositions comprising ketotifen and pharmaceutically acceptable salts thereof, as well as methods for making such compositions.

11 Claims, No Drawings

AUTOCLAVABLE PHARMACEUTICAL COMPOSITIONS CONTAINING A CHELATING AGENT

The present invention describes an autoclavable ophthalmic composition comprising an ophthalmic drug and in particular an ophthalmic drug. The invention further describes a method for stabilizing such compositions and the use of said stabilizers.

Drug safety is a permanent issue in drug regulatory affairs. A recent European regulation requires that a final ophthalmic composition must be autoclaved before use, and consequently, before sale. Autoclaving improves drug safety since the pathogenic germs are killed thereby.

JP 62/277323 describes for example a method for producing eye drops containing ketotifen fumarate, which eye drops might further contain a preservative such as benzalkonium chloride. In order to stabilize such a composition, JP 62/277323 proposes to add a polyvalent alcohol such as a saccharide and other alcohols such as glycerol or propylene glycol. The composition described is not stable if autoclaved.

Therefore the problem to be solved consists of providing in particular an aqueous ophthalmic composition comprising an ophthalmic drug, in particular selected from ketotifen and dexamethasone, which substantially prohibits decomposition when subjected to standard autoclaving conditions.

This problem had unexpectedly been solved by the addition of a stabilizer which is selected from the group consisting of EDTA, Dequest and Desferal. Preference is given to EDTA and Dequest and more particular to EDTA.

Another unexpected finding of the present invention is a synergistic effect, namely the effect of improved preservative efficacy if a preservative is added to said stabilized composition. This means that the amount preservative necessary to ensure shelf life and muti-dose sterility may be reduced very significantly, which in turn may strongly improve ocular tolerability of an addressed ophthalmic composition.

Consequently, the invention relates to an ophthalmic composition in accordance to the main claim. It further relates to the objects of all dependent and independent claims disclosed infra, in particular to a method of stabilizing an ophthalmic drug by adding a particular stabilizer during autoclavation.

According to the invention an ophthalmic composition is advantageously applied topically to the eye, especially in the form of a solution, a suspension or a gel. Such compositions comprise an ophthalmically effective ingredient and in particular ketotifen or dexamethasone, for example, in a range of from approximately 0.000001 to approximately 10.0% by weight, preferably from approximately 0.00001 to approximately 1.0% by weight, or more preferably in the range of from approximately 0.0001 to approximately 0.1% by weight and most preferably in the range of from 0.001 to 0.1% by weight. The dose of the active ingredient may depend on various factors, such as mode of administration, requirement, age and/or individual condition.

Other customary pharmaceutically acceptable excipients and additives known to the person skilled in the art are used in corresponding ophthalmic composition. Such compositions are prepared in a manner known per se, for example by mixing an active ingredient with the corresponding excipients and/or additives to form corresponding ophthalmic compositions.

Carriers used in accordance to the present invention are typically suitable for topical or general administration, and are for example water, mixtures of water and water-miscible solvents, such as $C_1$- to $C_7$-alkanols, vegetable oils or mineral oils comprising from 0.5 to 5% by weight hydroxyethylcellulose, ethyl oleate, carboxymethylcellulose, polyvinyl-pyrrolidone and other non-toxic water-soluble polymers for ophthalmic uses, such as, for example, cellulose derivatives, such as methylcellulose, alkali metal salts of carboxy-methylcellulose, hydroxymethylcellulose, hydroxyethylcellulose, methylhydroxypropyl-cellulose, hydroxypropylcellulose, chitosan and scleroglucan, acrylates or methacrylates, such as salts of polyacrylic acid or ethyl acrylate, polyacrylamides, natural products, such as gelatin, alginates, pectins, tragacanth, karaya gum, xanthan gum, carrageenin, agar and acacia, starch derivatives, such as starch acetate and hydroxypropyl starch, and also other synthetic products, such as poloxamers, e.g. Poloxamer F127, polyvinyl alcohol, polyvinylpyrrolidone, polyvinyl methyl ether, polyethylene oxide, preferably cross-linked polyacrylic acid, such as neutral Carbopol, or mixtures of those polymers. Preferred carriers are water, cellulose derivatives, such as methylcellulose, alkali metal salts of carboxymethylcellulose, hydroxymethylcellulose, hydroxyethylcellulose, methylhydroxypropylcellulose and hydroxypropylcellulose, neutral Carbopol, or mixtures thereof. The concentration of the carrier is, for example, from 0.1 to 100000 times the concentration of the active ingredient.

Solubilizers may be used for an ophthalmic composition of the present invention as well, and are, for example, tyloxapol, fatty acid glycerol polyethylene glycol esters, fatty acid polyethylene glycol esters, polyethylene glycols, glycerol ethers, polysorbate 20, polysorbate 80 or mixtures of those compounds. A specific example of an especially preferred solubilizer is a reaction product of castor oil and ethylene oxide, for example the commercial products Cremophor EL® or Cremophor RH40®. Reaction products of castor oil and ethylene oxide have proved to be particularly good solubilizers that are tolerated extremely well by the eye. Another preferred solubilizer is tyloxapol. The concentration used depends especially on the concentration of the active ingredient. The amount added is typically sufficient to solubilize the active ingredient. For example, the concentration of the solubilizer is from 0.1 to 5000 times the concentration of the active ingredient.

Buffers, tonicity enhancing agents and preservatives different from quaternary ammonium salts may be used in an ophthalmic composition of the present invention too.

Examples of buffer substances are acetate, ascorbate, borate, hydrogen carbonate/carbonate, citrate, gluconate, lactate, phosphate, propionate and TRIS (tromethamine) buffers. Tromethamine and borate buffer are preferred buffers. The amount of buffer substance added is, for example, that necessary to ensure and maintain a physiologically tolerable pH range. The pH range is typically in the range of from 4 to 9, preferably from 4.5 to 8.5 and more preferably from 5.0 to 8.2.

Tonicity enhancing agents may also be present in an above composition and are, for example of ionic and/or non-ionic type. Examples of ionic tonicity enhancers are e.g. alkali metal or earth metal halides, such as, for example, $CaCl_2$, KBr, KCl, LiCl, NaI, NaBr or NaCl, $Na_2SO_4$ or boric acid. Non-ionic tonicity enhancing agents are, for example, urea, glycerol, sorbitol, mannitol, propylene glycol, or dextrose. Typically, a sufficient amount of tonicity enhancing agent may be added to impart to an above ophthalmic composition an osmolality of approximately from 50 to 1000 mOsmol, preferred from 100 to 400 mOsmol, more preferred from 200 to 400 mOsmol and even more preferred from 250 to 350 mOsmol.

Preservatives may be present in an above composition too. A preservative may typically be selected from a quaternary ammonium compound such as benzalkonium chloride, benzoxonium chloride or the like. Benzalkonium chloride is better described as: N-benzyl-N—($C_8$–$C_{18}$alkyl)-N,N-dimethylammonium chloride. Examples of preservatives different from quaternary ammonium salts are alkyl-mercury salts of thiosalicylic acid, such as, for example, thiomersal, phenylmercuric nitrate, phenylmercuric acetate or phenylmercuric borate, parabens, such as, for example, methylparaben or propylparaben, alcohols, such as, for example, chlorobutanol, benzyl alcohol or phenyl ethanol, guanidine derivatives, such as, for example, chlorohexidine or polyhexamethylene biguanide, sodium perborate, Germal®II or sorbic acid. Preferred preservatives are quaternary ammonium compounds, in particular benzalkonium chloride, alkyl-mercury salts and parabens. Where appropriate, a sufficient amount of preservative is added to the ophthalmic composition to ensure protection against secondary contaminations during use caused by bacteria and fungi.

Another object of the present invention are autoclavable ophthalmic compositions in accordance to the specification and the claims, but with the proviso that the preservative is absent. Such compositions are in particular useful for the so called unidose forms.

An above ophthalmic composition may comprise further non-toxic excipients, such as, for example, emulsifiers, wetting agents or fillers, such as, for example, the polyethylene glycols designated 200, 300, 400 and 600, or Carbowax designated 1000, 1500, 4000, 6000 and 10000. Other excipients that may be used if desired are listed below but they are not intended to limit in any way the scope of the possible excipients. Such excipients are especially antioxidants, such as ascorbic acid, acetylcysteine, cysteine, sodium hydrogen sulfite, butyl-hydroxyanisole, butyl-hydroxytoluene or alpha-tocopherol acetate. The amount and type of excipient added is in accordance with the particular requirements and is generally in the range of from approximately 0.0001 to approximately 90% by weight.

Further excipients may be comprised in an above concerned ophthalmic composition, which may in particular function as a combined stabilizer/solubilizer. Such a combined additional stabilizer/solubilizer is for example a cyclodextrin. A preferred cyclodextrin is in particular selected from the group of α-cyclodextrin, β-cyclodextrin, γ-cyclodextrin, hydroxypropyl-β-cyclodextrin, hydroxypropyl-γ-cyclodextrin, dimethyl-β-cyclodextrin and dimethyl-γ-cyclodextrin. The amount is generally in the range of from approximately 0.01 to approximately 90% by weight, more preferably in the range of from 0.1–20% by weight.

Alkyl means throughout this invention an alkyl group having up to and including 18, more preferably 12 and even more preferably 7 C-atoms, and is either a linear or a branched alkyl group.

Examples for alkyl are methyl, ethyl, propyl, butyl, iso-propyl, t-butyl, neo-pentyl, octyl or dodecyl.

The term weight % used herein refers to the weight % of the total weight of an addressed composition or object.

The above is in particular useful for ophthalmic drugs. Examples of such ophthalmic drugs are antazolin, betaxolol, bupivacaine, carbachol, carteolol, chloramphenicol, chlortetracycline, cromolyn sodium, dexamethasone, dichlorphenamide, dipivefrin, ephedrine, erythromycin, fluoromethalone, indomethacin, ketotifen, levobunolol, levocabastine, lidocaine, lignocaine, lomefloxacin, medrysone, methazolamide, naphazoline, natamycin, neomycin, noradrenaline, ofloxacin, oxybuprocaine, physostigmine, pilocarpine, polymyxin B, prednisolone, scopolamine, sorbinil, sulfacetamide, tamoxifen, tetracaine, tetracycline, timolol, trifluridine, tropicamide, vidarabine, and ophthalmically acceptable salts, and mixtures thereof.

More preferred ophthalmic drug are selected from antazolin, betaxolol, chloramphenicol, dexamethasone, fluoromethalone, ketotifen, lomefloxacin, ofloxacin, pilocarpine, timolol and ophthalmically acceptable salts, and mixtures thereof.

Strongly preferred are ketotifen and dexamethasone.

The term ketotifen relates to the basic compound itself as well to any pharmaceutically acceptable salt thereof. A preferred pharmaceutically acceptable salt of ketotifen is for example a hydrochloride, a hydrobromide, a hydrogen maleate, a hydrogen sulfate and a hydrogen fumarate. A more preferred example is a hydrochloride and a hydrogen fumarate. Most preferred is a hydrogen fumarate.

Similarly, the term dexamethasone relates also e.g. to dexamethasone-21-acetate, dexamethasone-21-phosphate disodium salt, dexamethasone-21-dihydrogen phosphate disodium salt and the like. All these are known to the skilled person in the art and are specifically disclosed in Merck Index, 12th edition, page 498, No. 2986.

The term autoclaving relates to a standardized thermal heating procedure characterized by the following parameters:

Heating a test composition to 120° C. or more for a period of 15 minutes or more, wherein said composition is aqueous. Said aqueous composition is kept in a closed vessel, which vessel is typically a plastic or glass bottle. A preferred bottle material is polypropylene (PP). The pressure during autoclaving is typically 1 bar or more.

The autoclaving (autoclavation) may preferably range from 120–150° C., more preferably from 120–140° C.; the time needed may preferably range from 15–120 minutes, more preferably from 15–60 minutes; and the pressure applied may preferably range from 1–20 bar, more preferably from 1–10 bar, and even more preferably form 1–5 bar.

The term Dequest as used within the present invention relates to chelating agents having phosphonic acid or phosphonate groups. A preferred group of such chelating agents are organophosphonates, particularly amino tri(lower alkylene phosphonic acids). A variety of such chelating agents are commercially available from Monsanto Company, St. Louis, Mo., and are sold under the trademark DEQUEST®. Examples of such compounds include, without limitation, diethylene triamine penta(methylene phosphonic acid); hexamethylene-diaminetetra (methylenephosphonic acid); ethylenediaminetetra (methylenephosphonic acid); and aminotrimethylene phosphonates. A particularly preferred chelating agent is diethylene triamine penta(methylene phosphonic acid), sold under the trademark DEQUEST® 2060. Mixtures of such Requests mentioned above may be comprised too.

Within the terms of the present invention, EDTA relates to ethylendiamine tetraacetic acid itself as well to its various salts, namely e.g. to monosodium, disodium and/or potassium salts. EDTA may also be referred to as edetate. Mixtures of EDTA's may be comprised too.

Desferal relates within the present terms to deferoxamine itself (see Merck Index 12th edition, page 483, No. 2914) as well to its salts, e.g. hydrochloride, methanesulfonate and the like. Derivatives thereof, such as N-acetyldeferoxamine may also be comprised. Mixtures of such deferoxamines may be comprised too.

Typical examples which illustrate the present invention, but are not intended to limit it in any way, are described below.

EXAMPLE 1
Eye Drop Formulations

| eye drop formulations | | | | |
|---|---|---|---|---|
| ketotifen hydrogen fumarate | 0.069 mg | 0.069 mg | 0.069 mg | 0.069 mg |
| random methyl-β-cyclodextrin, | 2.000 g | 10.000 g | | |
| hydroxypropyl-γ-cyclodextrin | | | 2.000 g | 10.000 g |
| propylene glycol | 1.900 g | 1.900 g | 1.900 g | 1.900 g |
| disodium edetate | 0.050 g | 0.050 g | 0.050 g | 0.050 g |
| benzalkonium chloride | 0.010 g | 0.010 g | 0.010 g | 0.010 g |
| sodium hydroxide 1 N | q.s. | q.s. | q.s. | q.s. |
| water for injections ad | 100 ml | 100 ml | 100 ml | 100 ml |
| pH | 5.91 | 5.85 | 5.76 | 5.80 |
| Osmolality (mOsmol) | 287 | 292 | 292 | 295 |

EXAMPLE 2
Eye Drop Formulations

| eye drop formulations | | | | |
|---|---|---|---|---|
| ketotifen hydrogen fumarate | 0.069 mg | 0.069 mg | 0.069 mg | 0.069 mg |
| random methyl-β-cyclodextrin, | 2.000 g | 10.000 g | | |
| hydroxypropyl-γ-cyclodextrin | | | 2.000 g | 10.000 g |
| propylene glycol | 1.900 g | 1.900 g | 1.900 g | 1.900 g |
| disodium edetate | 0.050 g | 0.050 g | | |
| benzalkonium chloride | 0.010 g | 0.010 g | 0.010 g | 0.010 g |
| sodium hydroxide 1 N | q.s. | q.s. | q.s. | q.s. |
| water for injections ad | 100 ml | 100 ml | 100 ml | 100 ml |
| pH | 7.19 | 7.25 | 7.16 | 7.22 |
| Osmolality (mOsmol) | 277 | 285 | 283 | 290 |

EXAMPLE 3

Ketotifen 0.25% Eye Drops
Samples in 10 ml White-Colored PP-Bottles

| Composition (%) | A | B | Comparative |
|---|---|---|---|
| ketotifen hydrogen fumarate | 0.0345 | 0.0345 | 0.0345 |
| glycerol, pure compound | 2.550 | 2.125 | 2.125 |
| disodium edetate | 0.05 | 0.05 | — |
| benzalkonium chloride | 0.01 | 0.01 | 0.01 |
| sodium hydroxide 1 N | 0.083 | 0.080 | 0.074 |
| water for injection ad | 100 ml | 100 ml | 100 ml |
| 0-Value | | | |
| content of ketotifen hydrogen fumarate in % | 100.1 | 100.5 | 101.5 |
| pH | 5.31 | 5.29 | 5.32 |
| Osmolality (mOsmol) | 300 | 244 | 240 |
| Stresstest 15 hrs 80° C. | | | |
| content of ketotifen hydrogen fumarate in % | 100.4 | 98.7 | 99.4 |
| degradation products in % | n.d. | n.d. | 0.03 |
| pH | 5.28 | 5.24 | 5.27 |
| Osmolality (mOsmol) | 300 | 251 | 238 |
| Autoclaved, 120° C., 20 min., 1.5 bar pressure | | | |
| content of ketotifen hydrogen fumarate in % | 98.2 | | 96.5 |
| degradation products in % | n.d. | | 0.23 |
| pH | 5.31 | | 5.18 |
| Osmolality (mOsmol) | 299 | | 238 | n.d. = not detectable

EXAMPLE 4

Spersadex 0.1% Eye Drops

| Sample (Ingredients in g unless indicated differently) | A | B | C |
|---|---|---|---|
| dexamethasone sodium phosphate | 0.100 | 0.100 | 0.100 |
| boric acid | 1.800 | 1.800 | 1.800 |
| sodium borate | 0.250 | 0.250 | 0.250 |
| BAK (benzalkonium chloride) | 0.010 | 0.010 | 0.010 |
| Cremophor EL | 1.000 | 1.000 | 1.000 |
| HPMC (hydroxypropyl methylcellulose) | 0.200 | 0.200 | 0.200 |
| disodium edetate | — | 0.050 | — |
| Dequest 2060 | — | — | 0.013 |
| water for injection ad | 100 ml | 100 ml | 100 ml |
| O-Value | | | |
| % dexamethasone sodium phosphate | 101.4 | 101.7 | 101.5 |
| pH | 7.14 | 7.10 | 7.11 |
| Osmolality (mOsmol) | 313 | 323 | 316 |
| Autoclaved (10 ml PP-bottles, 120° C., 20 minutes, 1.5 bar) | | | |
| % dexamethasone sodium phosphate | 89.3 | 93.6 | 92.2 |
| pH | 7.15 | 7.13 | 7.14 |
| Osmolality (mOsmol) | 314 | 319 | 320 |
| Autoclaved (10 ml glass-bottles, 120° C., 20 minutes, 1.5 bar) | | | |
| % dexamethasone sodium phosphate | 88.4 | 93.3 | 92.0 |
| pH | 7.15 | 7.15 | 7.12 |
| Osmolality (mOsmol) | 317 | 321 | 317 |

EXAMPLE 5

| Ketotifen 0.025% Eye Drops. Samples in 5 ml white-colored PP-bottles | |
|---|---|
| Composition (%) | |
| ketotifen hydrogen fumarate | 0.0345 |
| glycerol, pure compound | 2.125 |
| disodium edetate | 0.05 |
| benzalkonium chloride | 0.01 |
| sodium hydroxide 1 N | 0.080 |
| water for injection ad | 100 ml |

|  | Stresstest | |
| --- | --- | --- |
|  | 0-Value | (1): 120° C., 15 bar, 20 min. and (2): 30° C., 3 month |
| ketotifen hydrogen fumarate | 99.5% | 98.3% |
| degradation products | n.d. | n.d. |
| pH | 5.25 | 5.27 |
| Osmolality | 238 mOsmol | 239 mOsmol |

The values before [0-value] and after the stresstest [(1): 120° C., 15 bar, 20 min. and (2): 30° C., 3 month] are within the standard deviation of the analytical method. This demonstrates the stability of the above ketotifen eye drops.

What is claimed is:

1. An ophthalmic pharmaceutical composition consisting essentially of 0.0345% ketotifen hydrogen fumarate, 2.125% glycerol, 0.01% benzalkonium chloride and water.

2. The composition according to claim 1 wherein the pH is between about 5.18 and about 5.32.

3. The composition according to claim 1 wherein the osmolality is about 240 milliosmoles.

4. The composition according to claim 2 wherein the osmolality is about 240 milliosmoles.

5. A method for making an ophthalmic pharmaceutical composition, comprising admixing the non-aqueous components ketotifen hydrogen fumarate, glycerol, and benzalkonium chloride with water such that a final concentration of the non-aqueous components is 0.0345% ketotifen hydrogen fumarate, 2.125% glycerol, and 0.01% benzalkonium chloride.

6. The method according to claim 5 wherein the pH of the composition is between about 5.18 and about 5.32.

7. The method according to claim 5 wherein the osmolality of the composition is about 240 milliosmoles.

8. The method according to claim 6 wherein the osmolality is about 240 milliosmoles.

9. The method according to claim 5 wherein the amount of degradation products in said composition is about 0.03%.

10. The composition according to claim 1 wherein the amount of degradation products in said composition is about 0.23%.

11. The composition according to claim 1 wherein the amount of degradation products in said composition is about 0.03%.

* * * * *

UNITED STATES PATENT AND TRADEMARK OFFICE
CERTIFICATE OF CORRECTION

PATENT NO. : 6,776,982 B2
DATED : August 17, 2004
INVENTOR(S) : Kis et al.

It is certified that error appears in the above-identified patent and that said Letters Patent is hereby corrected as shown below:

Title page,
Item [*] Notice, should read:
-- This patent is subject to terminal disclaimers. --

Signed and Sealed this

Fourteenth Day of December, 2004

JON W. DUDAS
*Director of the United States Patent and Trademark Office*